United States Patent [19]

Chibata et al.

[11] Patent Number: 4,463,094
[45] Date of Patent: Jul. 31, 1984

[54] FERMENTATION PRODUCTION OF L-THREONINE

[75] Inventors: Ichiro Chibata, Suita; Masahiko Kisumi, Kobe; Saburo Komatsubara, Kusatsu; Kousaku Murata, Kyoto, all of Japan

[73] Assignee: Tanabe Seiyaku Co., Ltd., Japan

[21] Appl. No.: 244,348

[22] Filed: Mar. 17, 1981

[30] Foreign Application Priority Data

Mar. 21, 1980 [JP] Japan .................................. 55-36777

[51] Int. Cl.$^3$ ...................... C12P 13/08; C12N 15/00; C12N 1/20; C12R 1/43
[52] U.S. Cl. ................................ 435/115; 435/172.1; 435/253; 435/881
[58] Field of Search ................ 435/115, 253, 172, 881

[56] References Cited

U.S. PATENT DOCUMENTS 3,732,144  5/1973  Nakayama et al. ................ 435/115

FOREIGN PATENT DOCUMENTS 893098  2/1972  Canada .............................. 435/115
52-7488  1/1977  Japan ................................ 435/115

OTHER PUBLICATIONS

Komatsubara et al., Applied Environ. Microbiol., 35 (5), 834–840, (1978).
Komatsubara et al., J. Bacter., 135 (2), 318–323, (1978).
Komatsubara et al., App. Environ. Microbiol., 38 (5), 777–782, (1979).
Komatsubara et al., App. Environ. Microbiol., 38 (6), 1045–1051, (1979).

*Primary Examiner*—Esther M. Kepplinger
*Attorney, Agent, or Firm*—Jordan B. Bierman; Linda Bierman

[57] ABSTRACT

An improved method for the fermentative production of L-threonine in a high yield, which comprises cultivating a methionine metabolism-antagonist resistant mutant of *Serratia marcescens* having L-threonine productivity in a broth to form and accumulate L-threonine therein and recovering accumulated L-threonine from the broth.

7 Claims, No Drawings

FERMENTATION PRODUCTION OF L-THREONINE

The present invention relates to the fermentative production of L-threonine.

In the fermentative production of L-threonine, as to microbes other than those belonging to the genus Serratia, it has been known to use mutants which require an amino acid relating to L-threonine biosynthesis or are resistant to a threonine metabolism-antagonist (Japanese Patent Publication Nos. 26708/1970, 33195/1971, 34193/1971, 34194/1971 and 44876/1973). As to microbes belonging to the genus Serratia, it has been also known to use mutants which lack a threonine-degrading enzyme and are resistant to a threonine metabolism-antagonist (Japanese Patent Publication No. 48195/1977). However, the conventional methods using these mutants are still insufficient to form and accumulate a large amount of L-threonine.

The main object of the present invention is to provide an improved method for the fermentative production of L-threonine. This object as well as other objects and advantages of the present invention will become apparent to those skilled in the art from the following description.

According to the present invention, there is provided a method for the fermentative production of L-threonine which comprises cultivating a methionine metabolism-antagonist resistant mutant of Serratia marcescens having L-threonine productivity in a broth to form and accumulate L-threonine therein and recovering accumulated L-threonine from the broth. It is believed that the formation and accumulation of L-threonine by a methionine metabolism-antagonist resistant mutant of a microbe belonging to the genus Serratia as is in the present invention have not been known heretofore in the prior art.

The mutant to be used in the present invention have bacteriological characteristics of Serratia marcescens as described in Bergey's Manual of Determinative Bacteriology 8th Edition, page 326 as well as L-threonine productivity and resistance to a methionine metabolism-antagonist (e.g. ethionine, norleucine, etc.).

The mutants to be used in the present invention may also be obtained by inducing mutation in parent strains such as known L-threonine-producing mutants of Serratia marcescens. Examples of the mutants useful as the parent strain are mutants having such mutation characteristics as requirement for various amino acids (e.g. isoleucine, lysine, methionine, diaminopimelic acid, etc.), resistance to amino acid analogs (e.g. hydroxynorvaline, S-2-aminoethylcysteine, etc.), deficiency of threonine-degrading enzymes (e.g. L-threonine dehydrogenase, L-threonine deaminase, etc.) or the like. Other known mutants which lack metabolic controls for threonine biosynthesis, for example, feedback inhibition of threonine-sensitive aspartokinase and homoserine dehydrogenase are also useful as the parent strains. Particularly suitable examples of the known mutants used as the parent strains are Serratia marcescens strain D-60 which is deficient in threonine-degrading enzymes (L-threonine dehydrogenase and L-threonine deaminase) and has isoleucine requirement [Journal of Bacteriology, Vol. 135, No. 2, pages 318–323 (1978)]; Serratia marcescens strain HNr53 which is deficient in threonine-degrading enzymes and has isoleucine requirement as well as hydroxynorvaline-resistance [Applied and Environmental Microbiology, Vol. 35, No. 5, pages 834–840 (1978)]; Serratia marcescens strain AECr301 which is deficient in threonine-degrading enzymes and has isoleucine requirement as well as hydroxynorvaline- and S-2-aminoethylcysteine-resistance [ibid., Vol. 38, No. 5, pages 777–782 (1979)]; Serratia marcescens strain T-570 which is deficient in threonine-degrading enzymes, has isoleucine requirement as well as hydroxynorvaline-resistance and lacks feedback inhibition of threonine-sensitive aspartokinase and homoserime dehydrogenase [ibid., Vol. 38, No. 6, pages 1045–1051 (1979)] or the like.

A representative example of the mutants to be used in the present invention is Serratia marcescens strain Sr41-P-103. This mutant was deposited with Fermentation Research Institute, Agency of Industrial Science and Technology, Japan (hereinafter referred to as FERM) on Feb. 25, 1980 under FERM-P No. 5413 and with American Type Culture Collection, U.S.A. (hereinafter referred to as ATCC) on Feb. 10, 1981 under ATCC No. 31809. This mutant was obtained from Serratia marcescens strain AECr301 and is resistant to ethionine being one of methionine metabolism-antagonists.

Other mutants obtained from the above known L-threonine-producing mutants by conventional mutagenizing treatments can also be used in the present invention. For example, there can be used a mutant obtained by irradiating the known mutant with ultraviolet or treating the mutant with a mutagen (e.g. N-methyl-N'-nitro-N-nitrosoguanidine, ethyl methanesulfonate, etc.) to provide a methionine metabolism antagonist resistance to the mutant, cultivating the resulting mutant at 30° C. for 2 to 4 days on agar plates (e.g. those of Davis's minimum medium) to which 1 to 20 mg/ml of a methionine metabolism-antagonist have been added and then picking up the resulting large colonies to isolate the desired mutant. More specifically, the desired ethionine-resistant mutant is produced as follows. The cells of the parent strain are treated with N-methyl-N'-nitro-N-nitrosoguanidine according to the method described by Adelberg et al., Biochem. Biophys. Res. Commun., Vol. 18, pages 788–795 (1965) to induce mutation in the cells. The resulting cells are spread on agar plates of a minimal medium containing glucose (0.5 w/v %), $(NH_4)_2SO_4$ (0.1 w/v %), $KH_2PO_4$ (0.3 w/v %), $K_2HPO_4$ (0.7 w/v %), $MgSO_4.7H_2O$ (0.01 w/v %) and isoleucine (0.01 w/v %) to which DL-ethionine 10 mg/ml is added and the plates are incubated at 30° C. for 4 days. The resulting large colonies are picked up to isolate the desired ethionine-resistant mutant.

If necessary, the above characteristics such as amino acid requirement, amino acid analog-resistance or lack of metabolic controls for threonine biosynthesis can be further provided to the mutants thus obtained by conventional mutagenizing treatments or transduction techniques. The thus obtained mutants can also be used in the present invention.

The broth to be used for the production of L-threonine in the present invention suitably contains 10 to 20 w/v % of a carbon source such as saccharides (e.g. glucose, sucrose, molasses, etc.), organic acids (e.g. fumaric acid, citric acid, etc.), alcohols (e.g. glycerol) or the like; 1 to 2 w/v % of a nitrogen source such as organic ammonium salts (e.g. ammonium acetate, etc.), inorganic ammonium salts (e.g. ammonium sulfate, ammonium chloride, etc.) urea or the like; and 0 to 1 w/v % of an organic nutrient such as corn steep liquor, peptone, yeast extract or the like. Further, a small amount of potassium phosphate, magnesium sulfate or the like may be added to the broth. Calcium carbonate or, if necessary, ammonia may also be added to the broth so as to maintain the pH thereof at 6 L to 8. Furthermore, a substance relating to threonine biosynthesis such as L-asparatic acid, L-homoserine, L-lysine, L-methionine, L-isoleucine or the like may also optionally be added to the broth.

According to the present invention, a large amount of L-threonine can be accumulated in the broth by inoculating the above methionine metabolism-antagonist resistant mutant into the broth and incubating at 25 to 37° C. for 2 to 6 days under good conditions for supplying oxygen, for example, with vigorous shaking. After completion of the fermentation, L-threonine is formed and accumulated in the broth. L-Threonine thus accumulated can readily be isolated and recovered from the culture broth by conventional separation and purification techniques such as those using an ion exchange resin.

The following example further illustrates the present invention but is not to be construed to limit the scope thereof.

EXAMPLE 1

A broth (pH 7.0, 15 ml) containing sucrose (17.5 L w/v %), $K_2HPO_4$ (0.1 w/v %), $MgSO_4.7H_2O$ (0.1 w/v %), $(NH_4)_2SO_4$ (0.05 w/v %), urea (1.75 w/v %), corn steep liquor (0.1 w/v %), L-methionine (0.1 w/v %) and calcium carbonate (1 w/v %) was placed in a 500 ml shaking flask and sterilized by autoclaving (Sucrose and L-methionine were separately sterilized and added to the broth aseptically).

Separately, Serratia marcescens strain Sr41-P-103 (FERM-P No. 5413, ATCC No. 31809) was incubated at 30° C. for 20 hours in a broth containing sucrose (12.5 w/v %), $K_2HPO_4$ (0.1 w/v %), $MgSO_4.7H_2O$ (0.1 w/v %), $(NH_4)_2SO_4$ (0.05 w/v %), urea (1.5 w/v %), corn steep liquor (0.1 w/v %), L-methionine (0.1 w/v %) and calcium carbonate (1 w/v %), and used as inoculum.

The culture of strain Sr41-P-103 (0.5 ml) was inoculated into the above-prepared broth and incubated at 30° C. for 120 hours with shaking (140 r.p.m., 7 cm stroke). After incubation, L-threonine was accumulated at a concentration of 45.4 mg/ml in the broth (L-threonine was detected by ninhydrin reaction on paper chromatogram of the broth and determined by bioassay using Leuconostoc mesenteroides strain P-60).

The resulting broth (1 liter) was collected, heated and filtered. The filtrate was passed through a column of Amberlite IR-120 (H-form) to adsorb L-threonine. The column was washed with water and eluted with 5% aqueous ammonia. The fractions containing L-threonine were collected, concentrated under reduced pressure, treated with charcoal and then filtered. Methanol was added to the filtrate and the resulting crude crystals were recrystallized form aqueous methanol to obtain L-threonine (35 g).

For comparison purpose, when Serratia marcescens strain AECr301 was cultivated according to the same procedure, L-threonine was accumulated at a concentration of 9.0 mg/ml in the broth.

REFERENCE EXAMPLE 1

Each strain shown in the following Table 1 was cultivated for 20 hours on nutrient agar slants and the cells grown on the slants were harvested and washed with physiological saline. The cells were suspended in physiological saline, inoculated into minimal medium (3 ml) (composition: glucose, 0.5 w/v %; $(NH_4)_2SO_4$, 0.1 w/v %; $KH_2PO_4$, 0.3 w/v %; $K_2HPO_4$, 0.7 w/v %; $MgSO_4.7H_2O$, 0.01 2 w/v %; and L-isoleucine, 0.01 w/v %) to which DL-ethionine was added in the concentration of 0, 1 or 10 mg/ml and incubated at 30° C. for 20 hours. The growth of each strain was observed. The results are shown in Table 1.

As is clear from Table 1, the growth of Serratia marcescens strain Sr41-P-103 (FERM-P No. 5413, ATCC No. 31809) used in the present invention was not inhibited at all even in the presence of ethionine in a high concentration. This shows that the strain had a high ethionine resistance.

TABLE 1

| | Relative growth (%)* | | |
|---|---|---|---|
| | DL-Ethionine concentration (mg/ml) | | |
| Strain | 0 | 1 | 10 |
| Serratia marcescens AECr301 | 100 | 24 | 5 |
| Serratia marcescens Sr41-P-103 | 100 | 103 | 107 |

*Relative growth (%) is expressed by determining the absorbence of each broth at 660 nm after cultivation and, with respect to each strain, calculating the ratio of the absorbance of the broth containing DL-ethionine to that without DL-ethionine by taking the latter as 100%.

What is claimed is:

1. A method for the fermentative production of L-threonine which comprises cultivating Serratia marcescens strain Sr 41-P-103, FERM-P 5413, ATCC 31809, in a broth, accumulating L-threonine therein, and recovering accumulated L-threonine.

2. A method according to claim 1 wherein the cultivation is carried out at pH 6 to 8.

3. A method according to claim 1, wherein the cultivation is carried out at 25° to 37° C.

4. A method according to claim 1, wherein the cultivation is carried out under aerobic conditions.

5. A method according to claim 1, wherein the broth contains 10 to 20 w/v % of a carbon source, 1 to 2 w/v % of a nitrogen source and 0 to 1 w/v % of an organic nutrient.

6. A method for the fermentative production of L-threonine which comprises cultivating Serratia marcescens strain Sr41-P-103 (FERM-P No. 5413, ATCC No. 31809) at 25° to 37° C. for 2 to 6 days in a broth containing 10 to 20 w/v % of a carbon source, 1 to 2 w/v % of a nitrogen source and 0 to 1 w/v % of an organic nutrient and being at pH 6 to 8 under aerobic conditions to form and accumulate L-threonine therein and recovering accumulated L-threonine from the broth.

7. A mutant strain of Serratia Marcescens which is strain Sr41-P-103, ATCC No. 31809, FERM-P No. 5413.

* * * * *